(12) United States Patent
Radulescu

(10) Patent No.: US 7,223,241 B2
(45) Date of Patent: May 29, 2007

(54) METHOD AND APPARATUS FOR ELASTICITY IMAGING

(75) Inventor: Emil G. Radulescu, New Haven, CT (US)

(73) Assignee: Aloka Co., Ltd. (JP)

( * ) Notice: Subject to any disclaimer, the term of this patent is extended or adjusted under 35 U.S.C. 154(b) by 93 days.

(21) Appl. No.: 11/014,320

(22) Filed: Dec. 16, 2004

(65) Prior Publication Data

US 2006/0173320 A1    Aug. 3, 2006

(51) Int. Cl.
*A61B 8/00*    (2006.01)
(52) U.S. Cl. .................................. 600/443; 600/438
(58) Field of Classification Search ........ 600/437–438, 600/440, 443, 447; 128/916; 73/573–575, 73/579, 596, 645
See application file for complete search history.

(56) References Cited

U.S. PATENT DOCUMENTS 6,508,768 B1 *    1/2003    Hall et al. .................. 600/443

OTHER PUBLICATIONS

Tsuyoshi Shiina et al., Clinical Assessment of Real-Time, Freehand Elasticity Imaging System Based on the Combined Autocorrelation Method, IEEE Ultrasonics Symposium, 2003, pp. 664-667.

Tomy Varghese et al., A Theoretical Framework for Performance Characterization of Elastography: the Strain Filter, IEEE Transactions on Ultrasonics, Ferroelectrics, and Frequency Control, Jan. 1, 1997, pp. 164-172, vol. 44, No. 1.
Brian S. Garra et al., Elastography of Breast Lesions: Initial Clinical Results, Breast Imaging, Jan. 1997, pp. 79-86.
Faouzi Kallel et al., Elastographic Imaging of Low-Contrast Elastic Modulus Distributions in Tissue, Ultrasound in Medicine and Biology, 1998, pp. 409-425, vol. 24, No. 3.
Thomas A. Krouskop et al., Elastic Moduli of Breast and Prostate Tissues under Compression, Ultrasonic Imaging, 1998, pp. 260-274.
Elisa E. Konofagou et al., Myocardial Elastography-A Feasibility Study in Vivo, Ultrasound in Medicine and Biology, 2002, p. 475-482, vol. 28, No. 4.
S. Srinivasan et al., Trade-Offs Between the Axial Resolution and the Signal-to-Noise Ratio in Elastography, Ultrasound in Medicine and Biology, 2003, pp. 847-866, vol. 29, No. 6.

* cited by examiner

*Primary Examiner*—Francis J. Jaworski
(74) *Attorney, Agent, or Firm*—Bachman & LaPointe, P.C.

(57) ABSTRACT

A computational efficient algorithm for compression analysis of free-hand static elasticity imaging performed using medical diagnostic ultrasound imaging equipment offers tissue compression quality and quantity feedback to the operator. The algorithm includes a criterion for automatic selection of the most advantageous pre- and post-compression frame pairs delivering elasticity images of optimal dynamic ranges (DR) and signal-to-noise ratios (SNR). The use of the algorithm in real time eases operator training and reduces significantly the amount of artifact in the elasticity images while lowering the computational burden.

57 Claims, 7 Drawing Sheets

METHOD AND APPARATUS FOR ELASTICITY IMAGING

BACKGROUND OF THE INVENTION

1. Field of the Invention

The present invention relates to a computational efficient algorithm for tissue compression analysis for free-hand static elasticity imaging. More specifically, this invention relates to an elasticity imaging system that employs medical diagnostic ultrasound imaging equipment to produce strain images.

2. Description of Related Art

It has been proved that pathological conditions often produce changes in biological tissue stiffness. Tumor tissues, for example, are known to exhibit mechanical properties different from the surrounding tissue, as indicated by the use of palpation as a diagnostic tool. Breast and prostate tumors are especially susceptible to changes in mechanical properties, as indicated in an article by T. A. Krouskop, T. M. Wheeler, F. Kallel, B. S. Garra, and T. Hall, entitled "Elastic moduli of breast and prostate tissues under compression.", Ultrasonic Imaging, 20:260–274, 1998, which is incorporated by reference herein.

Many cancers, such as scirrhous carcinoma of the breast, appear as extremely hard nodules. However, a lesion may or may not possess echogenic properties that would make it detectable with conventional diagnostic ultrasound imaging systems. Tumors of the prostate or the breast may thus be difficult to distinguish with conventional ultrasound techniques, yet may still be much stiffer than the surrounding tissue, as reported in an article by B. S. Garra, I Cespedes, J. Ophir, S. Spratt, R. A. Zuurbier, C. M. Magnant, and M. F. Pennanen, entitled "Elastography of breast lesions; initial clinical results," Radiology, 202:79–86, 1997, which is incorporated by reference herein. As the echogenity and the stiffness of tissue are in general uncorrelated, Garra et al. observe it is expected that imaging the hardness of the biological tissue will provide new information related to the pathological conditions, facilitating the diagnosis process.

The experimentally obtained elastic modulus data in normal and abnormal breast tissues at different frequencies and precompression strain levels was reported in the aforementioned article "Elastic moduli of breast and prostate tissues under compression." The data in the article shows that the differences between the elastic moduli of the various tissues of the breast may be useful in developing methods to distinguish between benign and malignant tumors. Tissues of the prostate were also examined as cancers of the prostate are also significantly stiffer than normal tissue. Similar data indicating differences between the elastic moduli for normal and abnormal prostate tissues were also reported.

The imaging modality that facilitates the display of mechanical properties of biological tissue is called elastography. The purpose of elastography is to display an image of the distribution of a physical parameter related to the mechanical properties of the tissue for clinical applications. In addition to the aforementioned breast and prostate applications of elastography, successful results have been reported for muscle and myocardial applications by F. Kallel, J. Ophir, K. Magee, and T. A. Krouskop, entitled "Elastographic imaging of low-contrast elastic modulus distributions in tissue.", Ultrasound in Med. & Biol, (409–425), 1998; E. E. Konofagou, J. D'Hooge, and J. Ophir, entitled "Myocardial elastography—a feasible study in vivo.", Ultrasound in Med. & Biol. 28(4):475–482, 2002, which is incorporated by reference herein.

Elasticity imaging consists of inducing an external or internal motion to the biological tissue and evaluating the response of the tissue using conventional diagnostic ultrasound imaging and correlation techniques. Depending on the imaging mode and on the nature of tissue motion, elasticity imaging applications are divided into three distinct categories: a) static elasticity (also known as strain-based, or reconstructive) that involves imaging internal motion of biological tissue under static deformation; b) dynamic elasticity (also known as wave-based) that involves imaging shear wave propagation through the tissue; and, c) mechanical elasticity (also known as stress-based and reconstructive) that involves measuring surface stress distribution of the tissue.

Each of the three elasticity imaging applications comprises three main functional components. First, the data are captured during externally or internally applied tissue motion or deformation. Second, the tissue response is evaluated, that is, displacement, strain, and stress are determined. Lastly, the elastic modulus of the tissue is reconstructed using the theory of elasticity. The last step involves implementing the theory of elasticity into modeling and solving the inverse problem from strain and boundary conditions to elastic modulus. As the boundary conditions and the modeling of theory of elasticity are highly dependent on the structure of the biological tissue, the implementation of the last step is rather cumbersome and typically not performed. Moreover, the evaluation and display of tissue strain in the second step is considered to deliver an accurate reproduction of the tissue's mechanical properties.

Static elasticity imaging application is the most frequently used modality. In this application, a small quasi-static compressive force is applied to the tissue using the ultrasound imaging transducer. The force can be applied either using motorized compression fixtures or using freehand scanning. The RF data before and after the compression are recorded to estimate the local axial and lateral motions using correlation methods. The estimated motions along the ultrasound propagation direction represent the axial displacement map of the tissue and are used to determine the axial strain map. The strain map is then displayed as a gray scale or color-coded image and is called an elastogram.

While the majority of the elasticity imaging work has been concentrated so far on off-line processing, proof of concept and method optimization, real-time oriented applications have been only recently reported by Y. Zhu and T. J. Hall, entitled "A modified block matching method for real-time freehand strain imaging.", Ultrasonic Imaging, 24:161–176, 2002, which is incorporated by reference herein; and by T. Shiina, M. Yamakawa, N. Nitta, E. Ueno, T. Matsumura, S. Tamano, and T. Mitake, entitled "Clinical assessment of real-time, freehand elasticity imaging system based on the combined autocorrelation method.", 2003 IEEE Ultrasonics Symposium, pages 664–667, which is incorporated by reference herein. The need for real-time elasticity imaging applications in clinical environment is primarily of a practical nature. However, real-time elasticity imaging is indeed needed to acquire and process the ultrasonic echo data in such a way that patient-scanning time is relatively low and diagnostically relevant elasticity images are produced immediately during the scan. Thus, such real-time elasticity imaging systems are capable of displaying ultrasonic B-mode images and strain images on the same screen in real-time. Such a display also facilitates the assessment of the clinical relevance of the strain images being obtained.

Furthermore, the real-time processing of the ultrasonic echo data allows for freehand compression and scanning of the biological tissue rather than utilizing bulky and slow motorized compression fixtures. Freehand compression, as opposed to motorized compression facilitates a more manageable and user-friendly scanning process and allows for a larger variety of scanning locations. Its disadvantage, however, consists of exhaustive operator training, as the sonographer constantly needs to adjust the compression technique to obtain strain images of good quality. In more detail, to obtain strain images of consistent dynamic range ("DR") and signal-to-noise ratio ("SNR"), the sonographer needs to maintain a constant compression rate while avoiding lateral and out-of-plane tissue motions. Moreover, the compression has to be performed exclusively on the axial direction of the imaging transducer while maintaining a certain speed and repetition period.

In short, due to the extremely complex nature of the tissue compression, obtaining elasticity images of consistent quality using free-hand strain imaging is neither trivial nor as expeditious as obtaining good quality B-mode images, thus real-time compression feedback is necessary to ensure proper operator training.

In an attempt to overcome the limitations discussed above, a few research groups proposed and implemented real-time static elasticity imaging systems as reported by Y. Zhu and T. J. Hall, entitled "A modified block matching method for real-time freehand strain imaging.", Ultrasonic Imaging, 24:161–176, 2002, which is incorporated by reference herein; and, by T. Shiina, M. Yamakawa, N. Nitta, E. Ueno, T. Matsumura, S. Tamano, and T. Mitake, entitled "Clinical assessment of real-time, freehand elasticity imaging system based on the combined autocorrelation method.", 2003 IEEE Ultrasonics Symposium, pages 664–667, which is incorporated by reference herein. In addition, U.S. Pat. No. 6,508,768 B1 to Hall et al. ("'768 patent") describes in detail a real-time static elasticity imaging procedure and implementation. However, those implementations disclosed by the '768 patent and the Zhu et al. and Shiina et al. articles do not account completely for all the limitations mentioned above.

More particularly, neither the articles by Zhu et al. and Shiina et al. nor the teachings of the '768 patent provide a quantitative indication of the compression quality being achieved by the operator. Moreover, the operator does not receive guidance in order to improve the compression quality when s/he is only provided strain images that may contain artifacts and poor SNR. One of several drawbacks being that possible artifacts present in the strain image cannot be qualitatively linked to poor compression quality. Additionally, the current implementations calculate and display strain images continuously, independently of the quality of the compression, or even in the absence of compression. Therefore the computational burden placed upon the imaging system is extremely high while only select sets of strain images faithfully indicate the mechanical properties of the imaged tissue and are artifact-free. Moreover, depending on the applied compression rate, strain images are displayed with variable (and less than optimal) DR and SNR, allowing for artifacts.

There exists a need for a computational efficient algorithm capable of providing real-time tissue compression quality and quantity feedback to the operator. There also exists a need for a computational efficient algorithm that automatically selects the most advantageous pre- and post-compression frame pairs for delivering elasticity images of optimal dynamic ranges and signal-to-noise ratios. There further exists a need for a computational efficient algorithm that generates compression quality feedback independently of the quality of the compression being achieved. There exists still yet a need for a computational efficient algorithm that measures, analyzes and visually displays both the axial and lateral displacements (negative and positive) of the decompression of tissue. There exists further still a need for a computational efficient algorithm that captures and archives all information utilized in generating the elasticity images for off-line analysis.

SUMMARY OF THE INVENTION

A method for performing elasticity imaging using an ultrasound system comprises setting a region of interest about an ultrasound image; compressing cyclically a biological tissue; acquiring at least one of a plurality of RF frame data at an imaging-relevant frame rate; analyzing at least one of the plurality of RF frame data using a compression feedback algorithm; displaying a comparison of a quantitative indication of at least one of the plurality of RF frame data across at least one displacement to a threshold value across at least one displacement; determining an acceptable compression value based upon the comparison; determining said compression is satisfactory; and displaying an elasticity image of said biological tissue at said imaging-relevant frame rate.

A method for performing elasticity imaging using an ultrasound system comprises setting a region of interest about an ultrasound image; compressing cyclically a biological tissue; acquiring at least one of a plurality of RF frame data at an imaging-relevant frame rate; analyzing at least one of the plurality of RF frame data using a compression feedback algorithm; displaying a comparison of a quantitative indication of at least one of the plurality of RF frame data across a cumulated axial displacement to a threshold value across the cumulated axial displacement; displaying a comparison of a quantitative indication of at least one of the plurality of RF frame data across a cumulated lateral displacement to a threshold value across the cumulated lateral displacement; determining an acceptable compression threshold value based upon the comparisons; determining the compression is satisfactory; generating an elasticity image of the biological tissue based upon the comparisons; and displaying the elasticity image of the biological tissue at the imaging-relevant frame rate.

An ultrasound elasticity imaging system comprises an ultrasound system in communication with a compression fixture; an elasticity imaging module in communication with the b-mode and strain imaging display unit; and a compression feedback algorithm capable of generating at an imaging relevant frame rate an elasticity image of a biological tissue integrated with the ultrasound system and in communication with the ultrasound system, the elasticity imaging module and the combined b-mode and strain imaging display unit.

An article of manufacture comprises a computer usable medium having a set of instruction means embodied therein for performing elasticity imaging on an ultrasound image, said computer usable medium comprising a set of instructions to set a region of interest about an ultrasound image using a compression fixture; a set of instructions to compress cyclically a biological tissue using the compression fixture; a set of instructions to acquire at least one of a plurality of RF frame data at an imaging-relevant frame rate; a set of instructions to analyze at least one of the plurality of RF frame data using a compression feedback algorithm; a set of instructions to display a comparison of a quantitative indication of at least one of the plurality of RF frame data across at least one displacement to a threshold value across at least one displacement; a set of instructions to determine an acceptable compression value based upon the comparison; and a set of instructions to display an elasticity image of the biological tissue at the imaging-relevant frame rate.

A program storage device readable by machine, tangibly embodying a program of instructions executable by the machine to perform method steps for performing elasticity imaging on an ultrasound image, comprises setting a region of interest about an ultrasound image using a compression fixture; compressing cyclically a biological tissue using the compression fixture; acquiring at least one of a plurality of RF frame data at an imaging-relevant frame rate; analyzing said at least one of said plurality of RF frame data using a compression feedback algorithm; displaying a comparison of a quantitative indication of at least one of the plurality of RF frame data across at least one displacement to a threshold value across the at least one displacement; determining an acceptable compression value based upon the comparison; and displaying an elasticity image of the biological tissue at the imaging-relevant frame rate.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
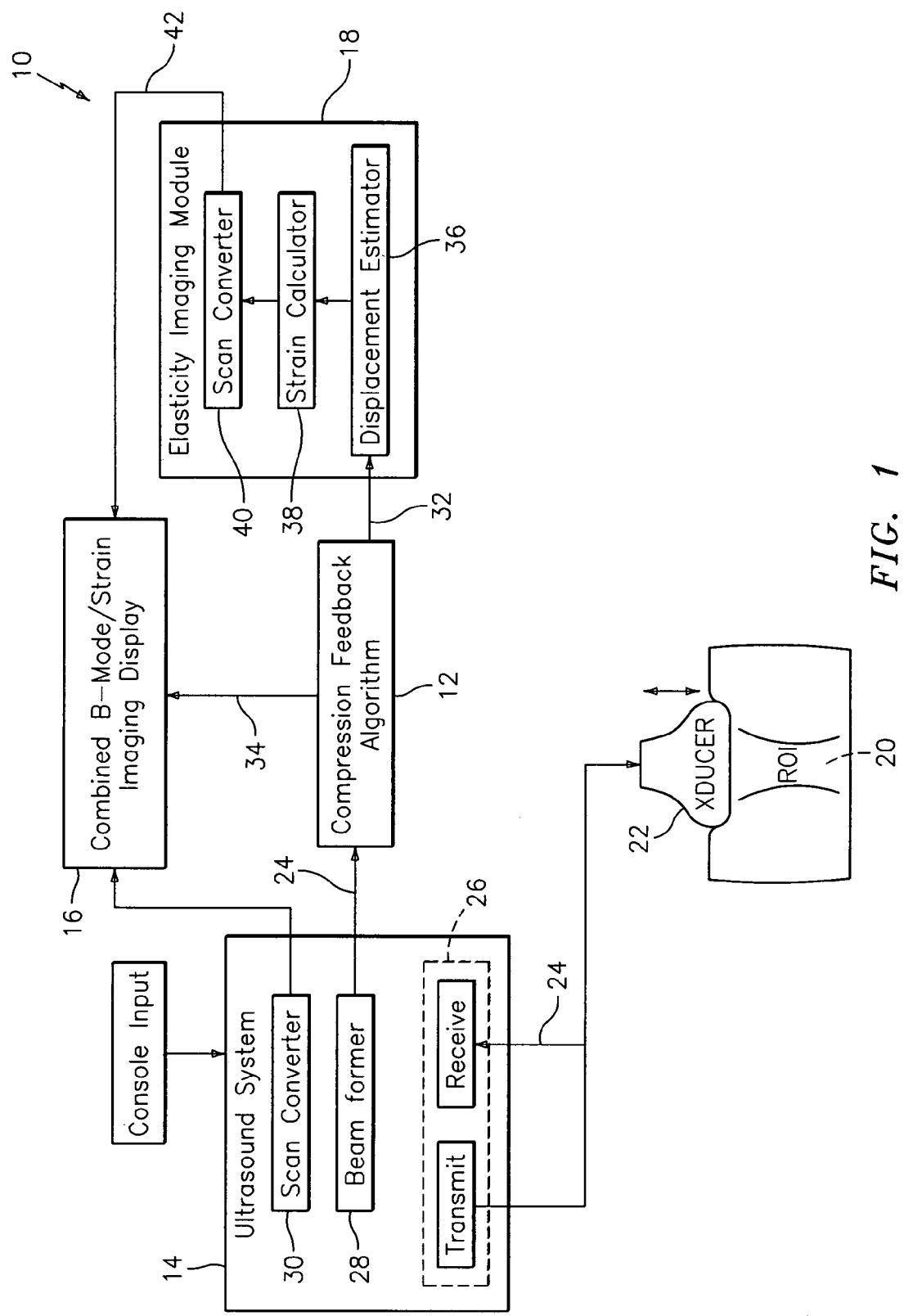
FIG. 1 is a block diagram of a real-time, free-hand static elasticity imaging system utilizing a diagnostic ultrasound system, incorporating a compression feedback algorithm of the present invention.

An elasticity imaging system, and method for using same, employs a tissue compression analysis algorithm for free-hand static elasticity imaging utilizing medical diagnostic ultrasound imaging equipment. The algorithm's application offers tissue compression quality and provides quantity feedback to the operator. The algorithm includes a criterion for the automatic selection of the most advantageous pre- and post-compression frame pairs for delivering elasticity images of optimal dynamic ranges and signal-to-noise ratios. In the alternative, the algorithm includes a criterion for the automatic selection of the most advantageous pre- and post-decompression decompression frame pairs for delivering elasticity images of optimal dynamic ranges and signal-to-noise ratios. The use of the algorithm in real time eases operator training and reduces significantly the amount of artifact in the elasticity images while also lowering the computational burden. In addition, operator training and confirmation of the quality of data behind the elasticity imaging results may be evaluated by displaying visually, alone or in combination, any and/or all of the qualitative, quantitative, and the like, data utilized in generating the elasticity images.

The algorithm initially considers the first frame of RF data received as the reference frame. The algorithm may then compare consecutive RF data frames using a block-matching process step. The block matching process step generally comprises applying an array measuring X number of rows and Y number of columns, where both X and Y may be, but are not limited to, odd numerals. This comparison may be executed utilizing a limited number of searching blocks.

The block matching algorithm is implemented using a normalized correlation technique, preferably a correlation coefficient technique. For each block, the search zone is limited to a small section of the following frame of RF data to speed up the execution. The search may be performed both axially and laterally. The motion of the blocks detected between consecutive frames may be given by the displacements corresponding to the lags that exhibit a maximum envelope of the correlation coefficient. The displacements found are cumulated from one frame pair to the next one. The quantitative indication of the tissue compression quality may be given by the maximum value of the envelope of the correlation coefficient. The quantitative data is averaged for the blocks positioned at the same depth in the ROI and are displayed for each individual depth considered. Preferably, the quantitative data is presented for three depths, corresponding to a top line, a middle line and a bottom line of the ROI.

The compression corresponding to a given RF frame data is accepted as valid once the quantitative indication exceeds a certain threshold, that is, the absolute value of the cumulated lateral displacement is smaller than a given threshold and the cumulated axial displacement is positive and smaller than a given threshold. Thus, a positive axial displacement indicates a compression motion rather than a decompression motion.

For an acceptable compression, if the cumulated axial displacement is larger than a preset imaging threshold, an originally stored RF reference frame and a given RF frame are sent to the static elasticity imaging module. The module calculates and displays a strain image in parallel with a B-Mode image of the RF reference frame. Then, the given RF frame is stored as a reference frame, the cumulated axial and lateral displacements are reinitialized and the algorithm restarts. If, however, the cumulated axial displacement is not larger than the preset imaging threshold, the algorithm is repeated for the next RF frame data cumulating the new displacements to the previously calculated ones.

On the other hand, if the compression is not acceptable, the given RF frame is stored as a reference, the cumulated axial and lateral displacements are reinitialized and the algorithm restarts without initiating a strain image display. The choice of the quantitative indication, lateral, and axial thresholds depends upon the B-Mode imaging parameters and the settings of the static elasticity imaging module.

As will be discussed in greater detail, an acceptable compression, or an acceptable decompression, may be quantitatively displayed as a set of points located within a range of acceptable threshold values. A compression motion may include a set of points indicating positive compression values. For a compression motion, a range may generally comprise a lower threshold boundary representing a minimum threshold value or imaging acceptable threshold value at which an acceptable strain image may be generated, and an upper threshold boundary representing a maximum threshold value or a largest acceptable threshold value at which an acceptable strain image may be generated. In contrast, a decompression may include a set of points indicating negative compression values. For decompression motion, a range for generating an acceptable strain image may generally comprise a lower threshold boundary representing a maximum threshold value or a largest acceptable threshold value, and an upper threshold boundary representing a minimum threshold value or an imaging acceptable threshold value.

A set of points comprising an acceptable compression, or an acceptable decompression, may be displayed across either an axial displacement or a lateral displacement, respectively. Likewise, a range of acceptable threshold values may also be displayed across either the axial displacement or the lateral displacement, respectively. Such a quantitative display may be generated for both positive compression values (compression motions) and negative decompression values (decompression motions). For example, FIGS. 4 through 8 illustrate quantitative displays of both acceptable and unacceptable compressions using positive compression values across an axial displacement.

The present invention, while herein described with respect to real-time, free-hand static elasticity imaging, is not so limited. Rather, a compression feedback algorithm may also be implemented in a static elasticity imaging system using motorized compression fixtures and off-line data processing. Additionally, with appropriate modifications contemplated herein, a compression feedback algorithm may be implemented in a dynamic elasticity imaging system.

Referring generally to FIGS. 1–8, in free-hand, real-time, static elasticity, the operator sets a region of interest (ROI) within a B-Mode image obtained from an ultrasound diagnostic system and compresses cyclically a biological tissue under investigation using, for example, an ultrasonic transducer probe. The ultrasound system acquires RF data in real-time, that is, at imaging-relevant frame rates, and sends it to the compression feedback algorithm.

Referring now to FIG. 1, the algorithm may be integrated in a static, free-hand, real-time elasticity imaging system 10. Elasticity imaging system 10 includes, in addition to compression feedback algorithm 12, the aforementioned diagnostic ultrasound system 14, a combined B-Mode/strain imaging display unit 16 and an elasticity imaging module 18.

In free-hand, real-time, static elasticity, the operator sets a region of interest ("ROI") 20 within a B-Mode image obtained from ultrasound diagnostic system 14, and compresses cyclically the tissue under investigation within the ROI using ultrasonic transducer probe 22. Ultrasound system 14 acquires RF data 24 at imaging-relevant frame rates, that is, in real-time, and sends RF data 24 to compression feedback algorithm 12.

Diagnostic ultrasound system 14 may include a console input (not shown), a transmit/receive hardware 26, as well as a beamformer module 28 and a scan converter module 30. The B-Mode images produced by scan converter 30 are sent to combined B-Mode/strain imaging display unit 16. Beamformer module 28 provides RF data in a continuous mode to compression feedback algorithm 12. Depending upon the compression quality and quantity, compression feedback algorithm 12 initiates an elasticity image by forwarding a select pair of RF data frames 32 to the elasticity imaging module 40. For each RF frame received, compression feedback algorithm 12 makes a sum of compression analysis parameters 34 available to combined B-Mode/strain imaging display 16.

Elasticity imaging module 18 may include a displacement estimator algorithm 36, a strain calculator module 38 and a scan converter 40. Displacement estimator module 36 assesses the tissue motion between RF data frames 32 received from the compression feedback algorithm 12. Strain calculator module 38 calculates the spatial derivative of the axial displacements and that result is transformed into a strain image 42 by elasticity imaging scan converter module 18. Finally, strain image 42 is sent to combined B-Mode/strain imaging display unit 16 that displays strain image 42 on a screen together with its corresponding B-Mode image.

Figure 2:
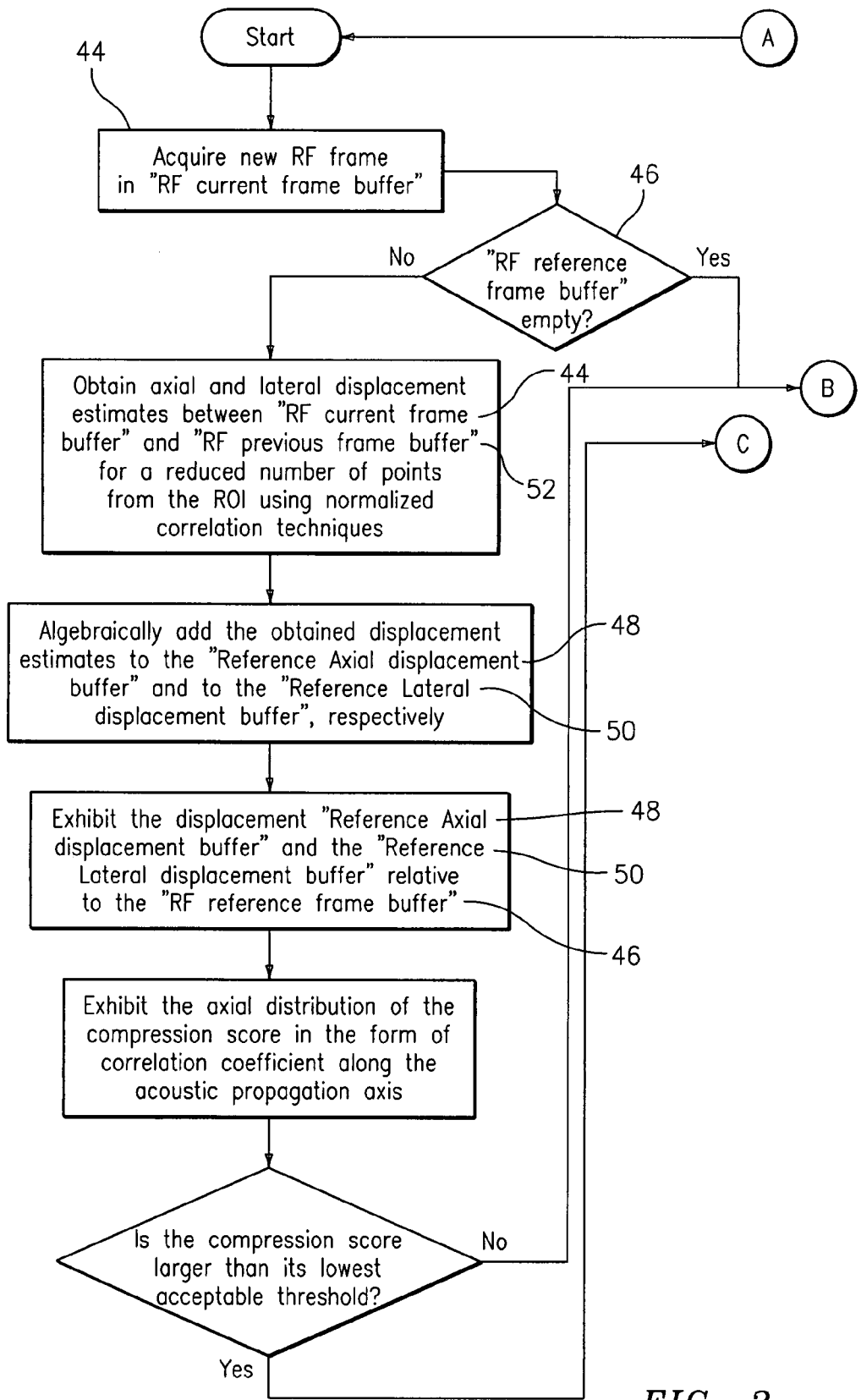
FIG. 2 a flowchart illustrating the main components and functionality of a compression feedback algorithm.
Figure 2:
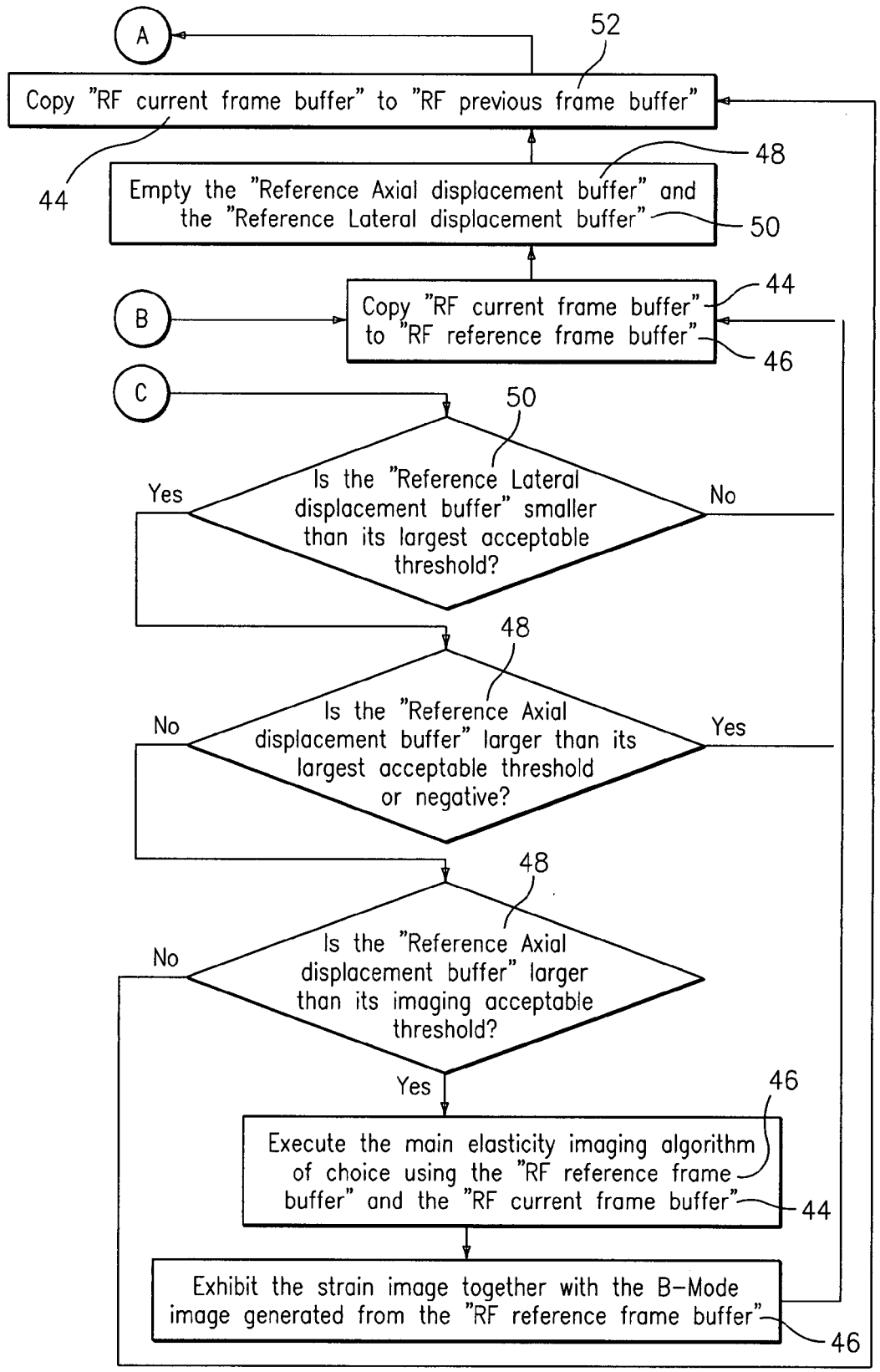

Referring now to FIG. 2, compression feedback algorithm 12 is illustrated as a flowchart. As shown, compression feedback algorithm 12 may include, but is not limited to, a plurality of buffers, each executing an instruction in order to perform algorithm 12. Table 1 generally describes the buffers, their respective functionalities and relations to one another within the execution of algorithm 12.

TABLE 1

| Buffer name | Buffer description |
| --- | --- |
| RF Current Frame | Buffer where the current RF frame data are stored. This buffer receives new data every time the algorithm restarts, independently on the quality of the compression. |
| RF Previous Frame | Buffer that contains the RF frame data acquired one step before the data from the RF Current Frame Buffer. This buffer receives new data every time the algorithm restarts, independently on the quality of the compression. |
| RF Reference Frame | Buffer that contains the reference RF frame data. This buffer receives new data when the algorithm runs for the first time, when the compression is considered unsatisfactory or after the execution of the elasticity imaging algorithm. |
| Reference Axial Displacement Buffer | Buffer that stores the cumulated axial tissue displacements detected between the data from the RF Current Frame Buffer and the RF Reference Frame Buffer. |
| Reference Lateral Displacement Buffer | Buffer that stores the cumulated lateral tissue displacements detected between the data from the RF Current Frame Buffer and the RF Reference Frame Buffer. |
| Compression Score | Buffer that stores the compression quantitative score between the data from the RF Current Frame Buffer and the RF Previous Frame Buffer. |

The starting point of the flowchart indicates the acquisition of a new RF data frame and storing the frame in the RF current frame buffer 44. As shown in Table 1, RF current frame buffer 44 may store the current, or the most recent, RF frame data 24 acquired, and preferably always stores the current RF frame data 24 acquired. The RF current frame buffer 44 receives new data every time compression feedback algorithm 12 restarts, independently of the quality of the compression.

Next, if the RF reference frame buffer 46 is empty, the data from the RF current frame buffer 44 is copied into it and algorithm 12 initializes its buffers and restarts with the acquisition of new RF frame data 24. The existence of the reference frame is therefore assured and algorithm 12 is initialized using the first frame of RF data received as the reference frame. A reference axial displacement buffer 48 and a reference lateral displacement buffer 50, which are initialized to zero if the RF reference frame buffer 46 is empty, store the cumulated axial and lateral displacements, respectively, as indicated in Table 1. These buffers 48, 50 correspond to the displacements detected between the data from RF current frame buffer 44 and RF reference frame buffer 46. RF previous frame buffer 52 may also be initialized with the data from RF current frame buffer 44 during this process. The RF previous frame buffer 52 may contain, and preferably always contains, RF frame data 24 acquired one step before (see Table 1). Similarly with RF current frame buffer 44, RF previous frame buffer 52 receives new data every time algorithm 12 restarts, independently of the quality of the compression.

As compression feedback algorithm 12 restarts and RF reference frame buffer 46 is not found empty, consecutive data frames may be compared using a block-matching algorithm (see FIG. 2.) The comparison is carried out between the data sets from RF previous frame buffer 52 and RF current frame buffer 44 and may be performed using only a limited number of searching blocks. For example, the block matching array may comprise a 3×3, 3×5, 5×3, 5×5, 3×7, 7×3, 7×5, 7×7, and the like, array of nine (9), fifteen (15), twenty-one (21), twenty-five (25), thirty-five (35), forty-nine (49), and the like, searching blocks. Preferably, the block-matching process step is performed using a 3×3 array placed over the center of the ROI such that the center search block of the array overlaps the center of the ROI.

The block-matching algorithm may be implemented using a normalized correlation technique, preferably a correlation coefficient technique. For each block, the search zone may be limited to a small section of the following frame of RF data to speed of the execution. The search may be performed both axially and laterally. Preferably, the search zone should be large enough to encompass the range of both axial and lateral displacements encountered between consecutive frames of RF data. By performing the search between consecutive RF data frames 24, rather than between the reference RF frame and the current RF frame, the search zone may be diminished significantly, thus increasing the algorithm computation speed. Additionally, the decorrelation between adjacent RF data frames 24 is much lower than between the reference RF frame and the current RF frame. The motion of the blocks detected between consecutive frames is given by the displacements corresponding to the lags that exhibit a maximum envelope of the correlation coefficient as known by one of ordinary skill in the art. While the displacements found are cumulated from one RF data frame pair to the next one, reference axial displacement buffer 48 for the axial displacements and reference lateral displacement buffer 50 for the lateral displacements are updated. Next, the updated values from reference axial displacement buffer 48 and reference lateral displacement buffer 50 may be sent to combined B-mode/strain imaging display module 16.

Figure 3:
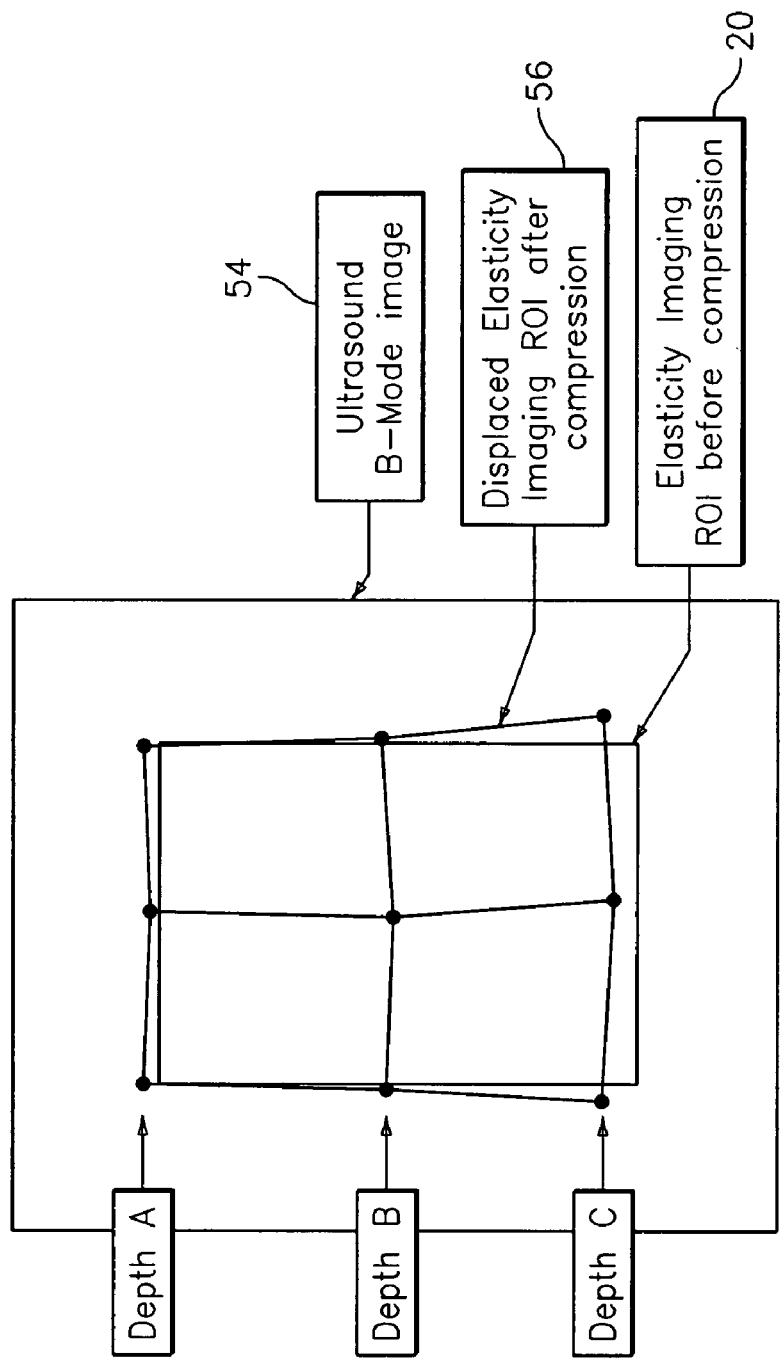
FIG. 3 a diagram of a B-Mode image display of an RF reference frame buffer, the elasticity imaging region of interest (ROI) before compression and an ROI after compression.

Referring now to FIG. 3, FIG. 3 illustrates a preferred embodiment of a combined B-mode/strain imaging display 16 of elasticity imaging system 10. The images created by reference axial displacement buffer 48 and reference lateral displacement buffer 50 may be superimposed onto B-mode image 54 created from RF frame data 24 contained in RF reference frame buffer 46. The selected elasticity imaging ROI before compression image 20 may be superimposed as a transparent, substantially rectangular shape onto B-mode image 54. The points for which the search is performed are displayed at the coordinates corresponding to the axial and lateral shifts contained in the reference axial displacement buffer 48 and the reference lateral displacement buffer 50, respectively. For the purpose of example, and not to be considered limiting, the points may be connected by twelve (12) lines, along the horizontal and vertical axes, which indicate a displaced elasticity imaging ROI after compression 56. The image shown in FIG. 3 gives the absolute coordinates of displaced ROI 20 and offers a visual indication of how large and in what direction the compression occurs. However, the axial and lateral displacements of the ROI 56 may be significantly smaller than the size of displaced ROI 20 and, thus, unapparent to the operator. This is why reference axial displacement buffer 48 is may also be displayed alone on combined B-mode/strain imaging display module 16.

Figure 4:
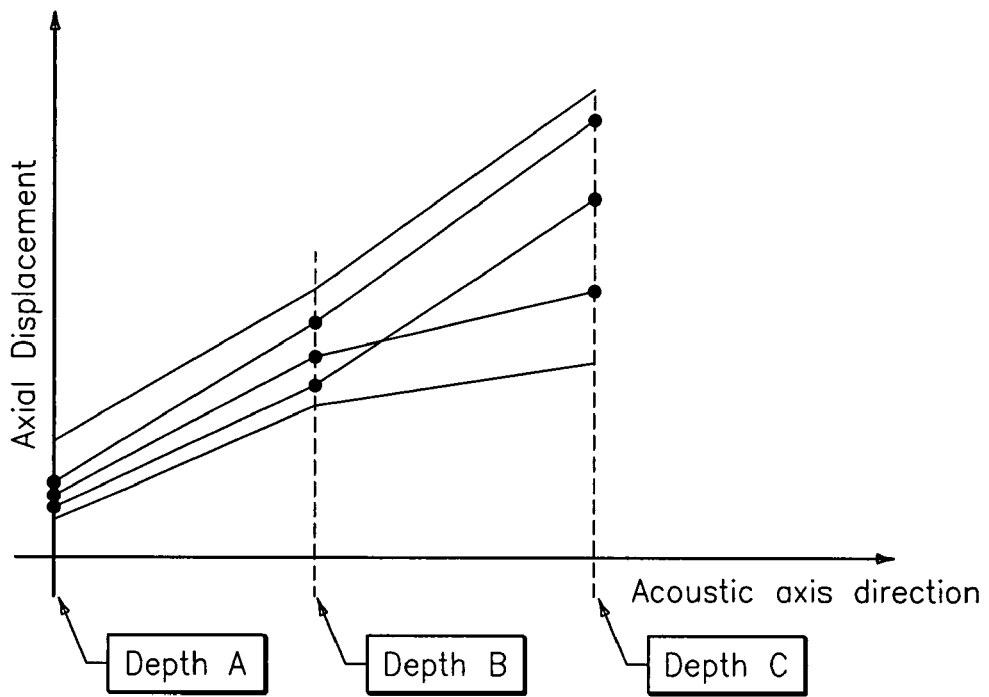
FIG. 4 a graph showing the cumulated axial displacement of an elasticity imaging ROI reference points for different depths along the acoustic axis.

Referring now to FIG. 4, FIG. 4 shows the preferred display of the reference axial displacement buffer 48. The horizontal axis represents the depth, and "Depth A", "Depth B" and "Depth C" corresponds to the depths marked on the vertical axis in FIG. 3. In FIG. 4 the azimuth direction is collapsed so that the points positioned at the same depth are displayed next to each other. The chart also shows a largest imaging acceptable threshold for the reference axial displacement buffer, which will be further discussed. Similar to the display of reference axial displacement buffer 48 in FIG. 4, reference lateral displacement buffer 50 may be shown in a similar fashion by collapsing the azimuth direction as is understood by one of ordinary skill in the art.

The quantitative indication of the tissue compression quality is stored in the Compression Score Buffer (see Table 1) and may be given by the maximum value of the envelope of the correlation coefficient for each of the nine searching blocks. The envelope of the correlation coefficient represents the envelope function of the correlation coefficient results obtained for all the positions where the search kernel was moved in the search zone prior to computing the correlation coefficient calculation. Calculating the envelope assures only positive values and eliminates fluctuations in the correlation coefficient results. The quantitative data may be averaged for the blocks positioned at the same depth in the ROI and may be displayed for each individual depth considered, as illustrated in FIG. 5.

Figure 5:
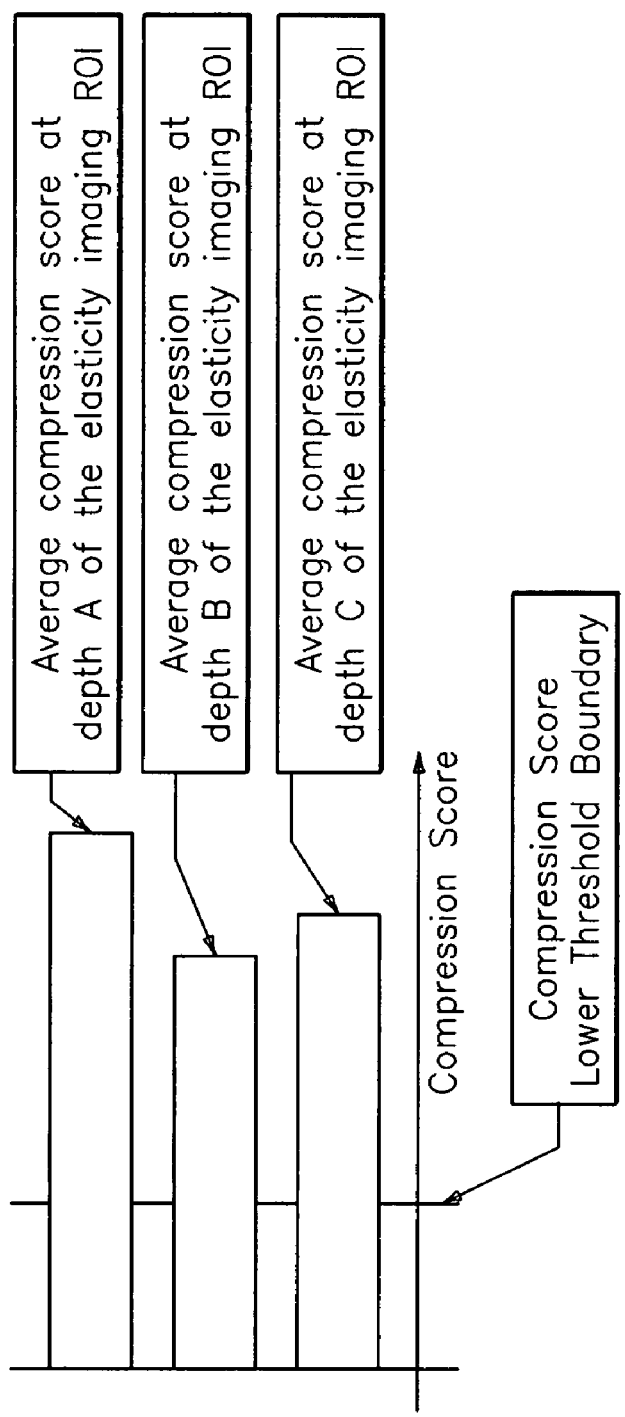
FIG. 5 is a chart showing the average quantitative indication of tissue compression quality for different depths.
Figure 7:
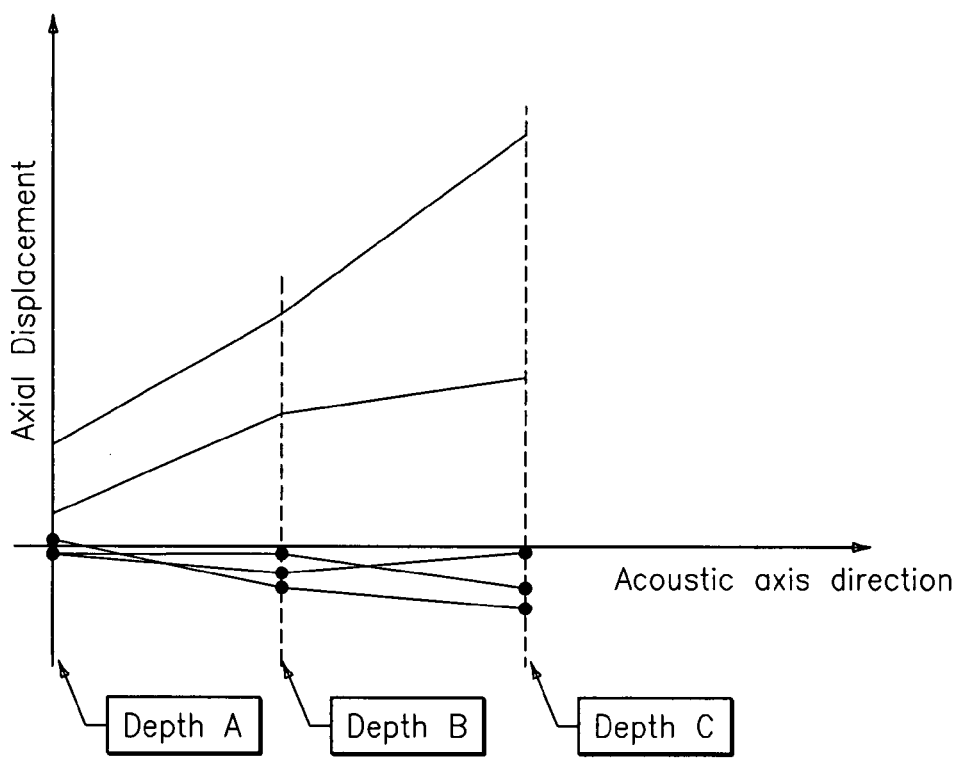
FIG. 7 is a graph depicting unacceptable compression as the axial displacement of several of the elasticity imaging reference points possess negative values.

Referring now to both FIGS. 3 and 5, in a preferred embodiment, the quantitative data may be presented for three depths corresponding to a top line ("Depth A"), a middle line ("Depth B") and a bottom line ("Depth C") of the ROI. The information displayed in FIGS. 3 and 5 is updated in real-time as new RF data frames 24 are acquired and made available to the compression feedback algorithm 12. Therefore, the information displayed provides real-time tissue compression quality and quantity feedback to the operator, and, additionally, the displayed information allows automatic selection of the most advantageous pre- and post-compression frame pairs. The automatic selection of the frame pairs lowers the computational burden as only selected frames are used for strain imaging calculations. The real-time display and automatic selection eases operator training and lowers the strain imaging computational burden.

Referring back to FIG. 2, a first automatic decision made with respect to the real-time tissue compression quality based upon quantitative data may be calculated using the records from the compression score buffer (see Table 1). Specifically, if the average compression score, at any depth, is lower than a compression score lowest acceptable threshold, the compression may be considered unacceptable and compression feedback algorithm 12 reinitializes the buffers and restarts with the acquisition to new RF frame data 24. A lowest acceptable threshold value of the compression score may be, on one hand, large enough to exclude one or more compression-based artifacts from the strain image(s) while, on the other hand, small enough to ensure an acceptable flux of strain images produced.

A second automatic decision based on quantitative data uses the reference lateral displacement buffer 50. If the absolute value of the lateral displacement of any of the points for which the search is performed is larger than a predefined maximum acceptable lateral threshold, the compression may be considered unacceptable and compression feedback algorithm 12 may reinitialize the buffers and restart with the acquisition of new RF frame data 24. A maximum acceptable lateral threshold value should be, on one hand, small enough to exclude the compression-based artifacts from the strain image(s) while, on the other hand, large enough to ensure an acceptable flux of strain images produced.

A third automatic decision based on quantitative date uses the Reference axial displacement buffer 48. If the value of the axial displacement of any of the points for which the search is performed is larger than a predefined maximum acceptable axial threshold, or negative, the compression may be considered unacceptable and the algorithm may reinitialize the buffers and restart with the acquisition of new RF frame data 24. Only positive axial displacements are accepted as they indicate compression motions, rather than decompression motions. In the alternative, negative axial displacements may be accepted so as to indicate decompression motions, rather than compression motions. Such an alternative embodiment may be employed to educate the operator, and/or generate a more complete elasticity imaging analysis of the tissue. Strain images could then be generated during decompression by measuring decompression motions against a negative imaging acceptable threshold and a negative largest acceptable threshold.

Figure 6:
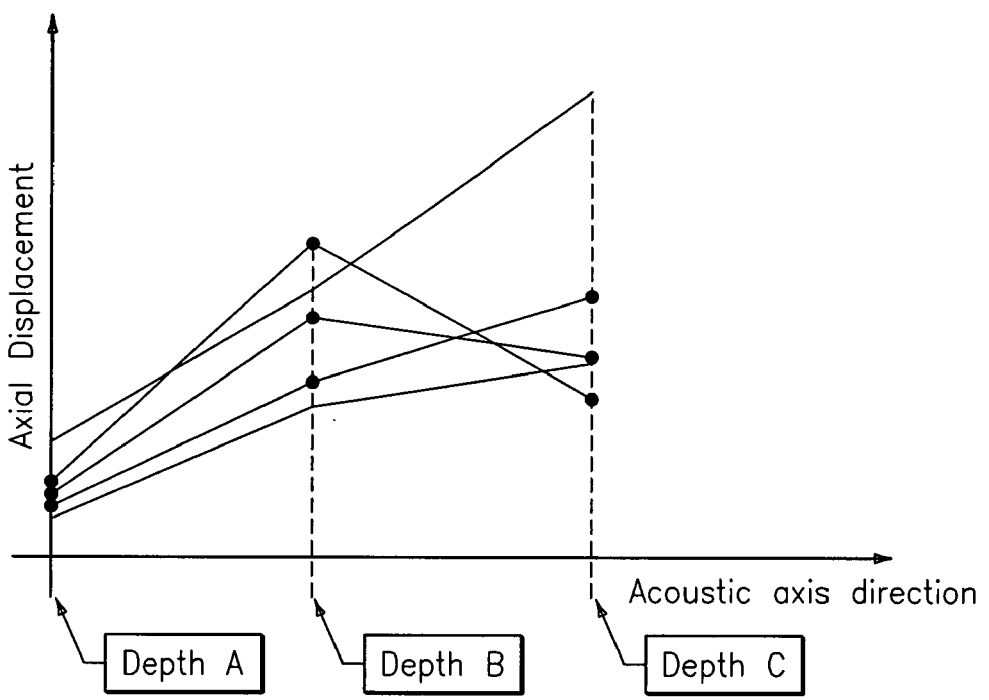
FIG. 6 is a graph depicting unacceptable compression as the axial displacement of one of the elasticity imaging reference points is greater than a predefined maximum acceptable axial threshold.

Referring now to FIG. 6, FIG. 6 illustrates an example when the value of the axial displacement of one of the points for which the search is performed is larger than the predefined maximum acceptable axial threshold, for example, Depth B, thus the compression is considered unacceptable. Similarly, FIG. 7 demonstrates another example when some of the axial displacements of the points for which the search is performed are negative and the compression is again considered unacceptable.

Figure 8:
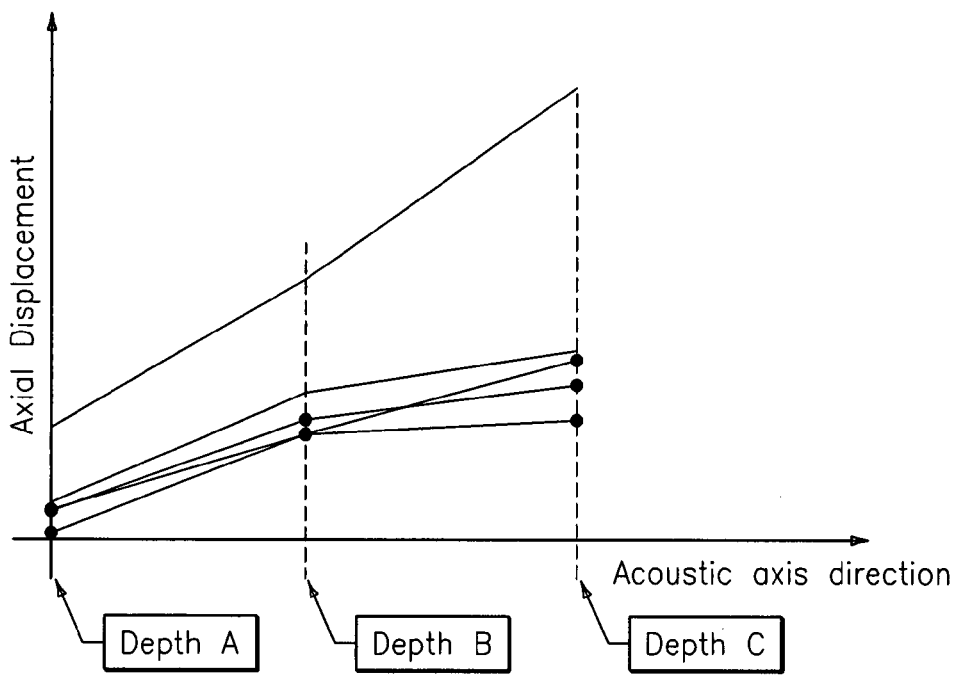
FIG. 8 is a graph depicting acceptable compression yet failing to produce good quality strain images due to axial displacements smaller than an imaging acceptable threshold.

Referring again to FIG. 2, a fourth automatic decision based on quantitative data may also use Reference axial displacement buffer 48. If the value of the axial displacement of any of the points for which the search is performed is smaller than the predefined imaging acceptable threshold, the compression may be considered acceptable but not large enough to produce good quality strain images as is illustrated in FIG. 8. In that event, the compression feedback algorithm may restart with the acquisition of new RF frame data 24 without reinitializing the buffers.

As further illustrated in FIG. 2, if the axial displacement of all the points for which the search is performed fall between a predefined imaging acceptable threshold and a predefined maximum acceptable axial threshold, the strain image may be calculated and displayed on combined B-Mode/strain imaging display unit 16 as demonstrated in FIG. 4. Subsequent to the strain imaging display, compression feedback algorithm 12 reinitializes the buffers and restarts with the acquisition of new RF frame data 24.

It should be noted that the positions of these thresholds with respect to depth, for example, Depth A, Depth B and Depth C, may establish the range of tissue strain at which the elasticity imaging is performed. The elasticity SNR typically exhibits a bandpass filter behavior in the strain domain as explained by T. Varghese and J. Ophir, "A theoretical framework for performance characterization of elastography: the strain filter.", IEEE Transactions on UFFC, 44(1): 164–172, 1997, which is incorporated herein by reference; and, by S. Srinivasan, R. Righetti and J. Ophir, "Trade-offs between the axial resolution and the signal-to-noise ratio in elastography.", Ultrasound in Med. & Biol, 29(6):847–966, 2003, which is incorporated herein by reference. Therefore, the proper choice of a tissue strain range ensures an adequate elasticity signal-to-noise ratio (SNR) and, thus, an optimal elasticity dynamic range (DR).

The strain imaging DR may be optimized by appropriately setting the predefined imaging acceptable threshold near a beginning of a passband region of the strain filter and also setting a predefined maximum acceptable axial threshold close to an end of the passband region of the strain filter. The selection of strain images, and elasticity images, appearing on a display of the elasticity imaging system will be optimized for elasticity SNR and optimal elasticity DR. Compression feedback algorithm 12 may act as a filter to determine and select such strain images for display using the elasticity imaging system. Such strain images may not only enhance the quality of the results obtained by an operator, but may also enhance the operator's training.

As mentioned earlier, operator training and confirmation of the quality of data behind the elasticity imaging results may be evaluated and feedback provided by the elasticity imaging system. Operator training may be accomplished using one or more different methods, including but not limited to, those discussed and contemplated herein.

For example, upon completion of generating an acceptable elasticity image, the operator can receive feedback with respect to the quality of his/her compressions and/or decompressions in generating the elasticity image. The statistical, qualitative, quantitative, and the like, data may be archived, e.g., historical data, such that the operator may recall the data to determine the quality of the compression or decompression and to provide feedback to the operator in order to improve his or her compression and/or decompression technique(s). More particularly, all of the statistical, quantitative, qualitative, and the like, historical or archived data utilized in generating the elasticity image, and each reference data frame used in composing the elasticity image, may be displayed in a statistical, quantitative, qualitative, and the like, diagram such as a table, chart, graph and the like, as known to one skilled in the art, with or without the elasticity image. For the purpose of example, and not to be limiting, such a diagram may comprise the graphs and charts of FIGS. 5–8, each alone or in combination with each other and/or the resultant elasticity image or pertinent reference data frame, arranged on a display unit for the operator, supervisor and the like.

The operator and/or supervisor may also receive feedback utilizing more than a diagram. For example, these diagrams may also include color and/or grayscale images of compression motions and/or decompression motions. An operator may determine the quality of a compression and/or a decompression by viewing a color change, or one or more color changes, occurring during a compression motion, e.g., the brightening of a darker area to a lighter area in a grayscale or color image, or the change in color from grayscale to color, and the like. A diagram exhibiting such color images and/or color changes may also be archived, e.g., historical data, and recalled during and/or after generating an elasticity image.

In addition to displaying archived or historical data using diagrams, audible noises may also be employed, and archived, to provide feedback to the operator. An audio recording and playback device may be integrated within elasticity imaging system 10, or may stand alone and be capable of capturing the audible noises produced while performing elasticity imaging. A noise may translate to a compression motion, a decompression motion, an acceptable compression/decompression motion, an unsatisfactory compression/decompression motion, and the like. Such noises may communicate information using one or more pitches, harmonics, volumes, rhythms, beats, combinations comprising at least one of the foregoing, and the like. The operator may hear such noises while compressing and decompressing a biological tissue and learn whether or not the motions fall within an acceptable compression/decompression range. Likewise, a supervisor may recall and listen to the recorded noise patterns to determine the quality of the compressions/decompressions performed by the operator. In turn, an operator may continue learning how to improve his/her skills by listening to an audio recording of his/her experimental runs using an elasticity imaging system contemplated herein.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A method for performing elasticity imaging using an ultrasound system, comprising:
    setting a region of interest about an ultrasound image;
    compressing cyclically a biological tissue;
    acquiring at least one of a plurality of RF frame data at an imaging-relevant frame rate;
    analyzing said at least one of said plurality of RF frame data using a compression feedback algorithm;
    displaying a comparison of a quantitative indication of said at least one of said plurality of RF frame data across at least one displacement to a threshold value across said at least one displacement;
    determining an acceptable compression value based upon said comparison;
    determining said compression is satisfactory; and
    displaying an elasticity image of said biological tissue at said imaging-relevant frame rate.

2. The method of claim 1, wherein setting said region of interest comprises applying a freehand compression fixture to said biological tissue.

3. The method of claim 2, wherein applying said freehand compression fixture comprises applying an ultrasonic transducer probe.

4. The method of claim 1, wherein setting said region of interest comprises applying a motorized compression fixture.

5. The method of claim 1, wherein analyzing said at least one of said plurality of RF frame data using said compression feedback algorithm comprises
    selecting a first RF frame data of said plurality of RF frame data as a reference RF frame for said plurality of RF frame data;
    comparing said plurality of RF frame data following said reference RF frame with said reference RF frame using a block matching algorithm;
    performing said comparison step across an axial displacement and a lateral displacement;
    determining a quantitative indication of a tissue compression quality for each of said plurality of RF frame data across a lateral displacement and an axial displacement; and
    averaging said quantitative indications for said plurality of RF frame data across said lateral displacement and said axial displacement and generating a cumulated lateral displacement and a cumulated axial displacement for said plurality of RF frame data.

6. The method of claim 1, wherein displaying visually said comparison comprises
    displaying a comparison of a cumulated lateral displacement for said plurality of RF frame data to a threshold value across a lateral displacement; and
    displaying a comparison of a cumulated axial displacement for said plurality of RF frame data to a threshold value across an axial displacement.

7. The method of claim 1, wherein determining said acceptable compression value comprises
    achieving an acceptable compression when an absolute value of a cumulated lateral displacement for said plurality of RF frame data is less than a threshold value across said lateral displacement, and a cumulated axial displacement for said plurality of RF frame data is less than an upper threshold boundary and greater than a lower threshold boundary across an axial displacement.

8. The method of claim 1, wherein determining said acceptable compression value comprises
    achieving an acceptable compression when an absolute value of a cumulated lateral displacement for said plurality of RF frame data is less than a threshold value across said lateral displacement, and a cumulated axial displacement for said plurality of RF frame data is less than a lower threshold boundary across an axial displacement, wherein said cumulated axial displacement is a positive value.

9. The method of claim 1, wherein determining said acceptable compression value comprises
    achieving an acceptable compression when an absolute value of a cumulated lateral displacement for said plurality of RF frame data is less than a threshold value across said lateral displacement, and a cumulated axial displacement for said plurality of RF frame data is greater than a lower threshold boundary and less than an upper threshold boundary across an axial displacement, wherein said cumulated axial displacement is a negative value.

10. The method of claim 1, wherein determining said acceptable compression value comprises
    achieving an acceptable compression when an absolute value of a cumulated lateral displacement for said plurality of RF frame data is less than a threshold value across said lateral displacement, and a cumulated axial displacement for said plurality of RF frame data is greater than an upper threshold boundary across an axial displacement, wherein said cumulated axial displacement is a negative value.

11. The method of claim 1, further comprising displaying one or more statistical, quantitative and qualitative diagrams of data of said elasticity image and of said at least one of said plurality of RF frame data.

12. The method of claim 1, further comprising displaying one or more statistical, quantitative or qualitative diagrams of data of said elasticity image and of said at least one of said plurality of RF frame data.

13. The method of claim 1, further comprising displaying one or more statistical, quantitative and qualitative diagrams of data of said elasticity image or of said at least one of said plurality of RF frame data.

14. The method of claim 1, further comprising displaying one or more statistical, quantitative or qualitative diagrams of data of said elasticity image or of said at least one of said plurality of RF frame data.

15. The method of claim 1, further comprising archiving said at least one of said plurality of RF frame data and said elasticity image.

16. The method of claim 1, further comprising generating an audio recording of each of said steps and storing said audio recordings.

17. The method of claim 1, further comprising decompressing cyclically said biological tissue.

18. The method of claim 1, further comprising the additional step of generating an elasticity image of said biological tissue based upon achieving an acceptable compression prior to displaying said elasticity image.

19. A method for performing elasticity imaging using an ultrasound system, comprising:
    setting a region of interest about an ultrasound image;
    compressing cyclically a biological tissue;
    acquiring at least one of a plurality of RF frame data at an imaging-relevant frame rate;
    analyzing said at least one of said plurality of RF frame data using a compression feedback algorithm;
    displaying a comparison of a quantitative indication of said at least one of said plurality of RF frame data across a cumulated axial displacement to a threshold value across said cumulated axial displacement;
    displaying a comparison of a quantitative indication of said at least one of said plurality of RF frame data across a cumulated lateral displacement to a threshold value across said cumulated lateral displacement;
    determining an acceptable compression threshold value based upon said comparisons;
    determining said compression is satisfactory;
    generating an elasticity image of said biological tissue based upon said comparisons; and
    displaying said elasticity image of said biological tissue at said imaging-relevant frame rate.

20. An ultrasound elasticity imaging system, comprising:
    an ultrasound system in communication with a compression fixture;
    an elasticity imaging module in communication with said b-mode and strain imaging display unit; and
    means for providing feedback predicting a strain image quality related to a tissue compression quality prior to computing a strain image, said means for providing feedback is in communication with said ultrasound system, said elasticity imaging module and said combined b-mode and strain imaging display unit.

21. The ultrasound elasticity imaging system of claim 20, wherein said compression fixture is a freehand compression fixture.

22. The ultrasound elasticity imaging system of claim 20, wherein said compression fixture is a motorized compression fixture.

23. The ultrasound elasticity imaging system of claim 20, wherein ultrasound system comprises a combined transmission and reception hardware, a beamformer module and a scan converter module.

24. The ultrasound elasticity imaging system of claim 20, wherein said elasticity imaging module comprises a displacement estimator algorithm, a strain calculator module and a scan converter.

25. The ultrasound elasticity imaging system of claim 20, further comprising a display unit capable of displaying one or more statistical, quantitative and qualitative diagrams of data of said elasticity and of said at least one of said plurality of RF frame data.

26. The ultrasound elasticity imaging system of claim 20, wherein said means for providing feedback comprises a compression feedback algorithm capable of generating at an imaging relevant frame rate an elasticity image of a biological tissue integrated with said ultrasound system.

27. An apparatus for performing elasticity imaging on an ultrasound image, comprising a set of instructions for performing elasticity imaging embodied in a computer readable storage medium of an ultrasound elasticity imaging system, wherein said set of instructions comprise:
    an instruction to set a region of interest about an ultrasound image using a compression fixture;
    an instruction to compress cyclically a biological tissue using said compression fixture;
    an instruction to acquire at least one of a plurality of RF frame data at an imaging-relevant frame rate;
    an instruction to analyze said at least one of said plurality of RF frame data using means for providing feedback predicting a strain image quality related to a tissue compression quality prior to computing a strain image;
    an instruction to display a comparison of a quantitative indication of said at least one of said plurality of RF frame data across at least one displacement to a threshold value across said at least one displacement;
    an instruction to determine an acceptable compression value based upon said comparison;
    an instruction to determine said compression is satisfactory; and
    an instruction to display an elasticity image of said biological tissue at said imaging-relevant frame rate.

28. The apparatus of claim 27, wherein said instruction to analyze comprises
    an instruction to select a first RF frame data of said plurality of RF frame data as a reference RF frame for said plurality of RF frame data;
    an instruction to compare said plurality of RF frame data following said reference RF frame with said reference RF frame using a block matching algorithm;
    an instruction to perform said comparison step across an axial displacement and a lateral displacement;
    an instruction to determine a quantitative indication of a tissue compression quality for each of said plurality of RF frame data across a lateral displacement and an axial displacement; and
    an instruction to average said quantitative indications for said plurality of RF frame data across said lateral displacement and said axial displacement and generating a cumulated lateral displacement and a cumulated axial displacement for said plurality of RF frame data.

29. The apparatus of claim 27, wherein said instruction to display visually said comparison comprises
an instruction to display a comparison of a cumulated lateral displacement for said plurality of RF frame data to a threshold value across a lateral displacement; and
an instruction to display a comparison of a cumulated axial displacement for said plurality of RF frame data to a threshold value across an axial displacement.

30. The apparatus of claim 27, wherein said instruction to determine said acceptable compression value comprises
an instruction to achieve an acceptable compression when an absolute value of a cumulated lateral displacement for said plurality of RF frame data is less than a threshold value across said lateral displacement, and a cumulated axial displacement for said plurality of RF frame data is less than an upper threshold boundary and greater than a lower threshold boundary across an axial displacement.

31. The apparatus of claim 27, wherein said instruction to determine said acceptable compression value comprises
an instruction to achieve an acceptable compression when an absolute value of a cumulated lateral displacement for said plurality of RF frame data is less than a threshold value across said lateral displacement, and a cumulated axial displacement for said plurality of RF frame data is less than a lower threshold boundary across an axial displacement, wherein said cumulated axial displacement is a positive value.

32. The apparatus of claim 27, wherein said instruction to determine said acceptable compression value comprises
an instruction to achieve an acceptable compression when an absolute value of a cumulated lateral displacement for said plurality of RF frame data is less than a threshold value across said lateral displacement, and a cumulated axial displacement for said plurality of RF frame data is greater than a lower threshold boundary and less than an upper threshold boundary across an axial displacement, wherein said cumulated axial displacement is a negative value.

33. The apparatus of claim 27, wherein said instruction to determine said acceptable compression value comprises
an instruction to achieve an acceptable compression when an absolute value of a cumulated lateral displacement for said plurality of RF frame data is less than a threshold value across said lateral displacement, and a cumulated axial displacement for said plurality of RF frame data is greater than an upper threshold boundary across an axial displacement, wherein said cumulated axial displacement is a negative value.

34. The apparatus of claim 27, further comprising an instruction to generate an elasticity image of said biological tissue based upon achieving an acceptable compression prior to executing said instruction to display said elasticity image.

35. The apparatus of claim 27, further comprising an instruction to display one or more statistical, quantitative and qualitative diagrams of data of said elasticity image and of said at least one of said plurality of RF frame data.

36. The apparatus of claim 27, further comprising an instruction to display one or more statistical, quantitative or qualitative diagrams of data of said elasticity image and of said at least one of said plurality of RF frame data.

37. The apparatus of claim 27, further comprising an instruction to display one or more statistical, quantitative and qualitative diagrams of data of said elasticity image or of said at least one of said plurality of RF frame data.

38. The apparatus of claim 27, further comprising an instruction to display one or more statistical, quantitative or qualitative diagrams of data of said elasticity image or of said at least one of said plurality of RF frame data.

39. The apparatus of claim 27, further comprising an instruction to archive said at least one of said plurality of RF frame data and said elasticity image.

40. The apparatus of claim 27, further comprising an instruction to generate an audio recording of each of said steps and store said audio recordings.

41. The apparatus of claim 27, further comprising an instruction to decompress cyclically said biological tissue.

42. An article of manufacture, comprising:
a computer usable medium having a set of instruction means embodied therein for performing elasticity imaging on an ultrasound image, said computer usable medium comprising:
a set of instructions to set a region of interest about an ultrasound image using a compression fixture;
a set of instructions to compress cyclically a biological tissue using said compression fixture;
a set of instructions to acquire at least one of a plurality of RF frame data at an imaging-relevant frame rate;
a set of instructions to analyze said at least one of said plurality of RF frame data using a compression feedback algorithm;
a set of instructions to display a comparison of a quantitative indication of said at least one of said plurality of RF frame data across at least one displacement to a threshold value across said at least one displacement;
a set of instructions to determine an acceptable compression value based upon said comparison; and
a set of instructions to display an elasticity image of said biological tissue at said imaging-relevant frame rate.

43. The article of manufacture of claim 42, wherein said set of instructions to analyze comprises
a set of instructions to select a first RF frame data of said plurality of RF frame data as a reference RF frame for said plurality of RF frame data;
a set of instructions to compare said plurality of RF frame data following said reference RF frame with said reference RF frame using a block matching algorithm;
a set of instructions to perform said comparison step across an axial displacement and a lateral displacement;
a set of instructions to determine a quantitative indication of a tissue compression quality for each of said plurality of RF frame data across a lateral displacement and an axial displacement; and
a set of instructions to average said quantitative indications for said plurality of RF frame data across said lateral displacement and said axial displacement and generating a cumulated lateral displacement and a cumulated axial displacement for said plurality of RF frame data.

44. The article of manufacture of claim 42, wherein said set of instructions to display visually said comparison comprises
a set of instructions to display a comparison of a cumulated lateral displacement for said plurality of RF frame data to a threshold value across a lateral displacement; and
a set of instructions to display a comparison of a cumulated axial displacement for said plurality of RF frame data to a threshold value across an axial displacement.

45. The article of manufacture of claim 42, wherein said set of instructions to determine said acceptable compression value comprises
a set of instructions to achieve an acceptable compression when an absolute value of a cumulated lateral displacement for said plurality of RF frame data is less than a threshold value across said lateral displacement, and a cumulated axial displacement for said plurality of RF frame data is less than an upper threshold boundary and greater than a lower threshold boundary across an axial displacement.

46. The article of manufacture of claim 42, wherein said set of instructions to determine said acceptable compression value comprises
a set of instructions to achieve an acceptable compression when an absolute value of a cumulated lateral displacement for said plurality of RF frame data is less than a threshold value across said lateral displacement, and a cumulated axial displacement for said plurality of RF frame data is less than a lower threshold boundary across an axial displacement, wherein said cumulated axial displacement is a positive value.

47. The article of manufacture of claim 42, wherein said set of instructions to determine said acceptable compression value comprises
a set of instructions to achieve an acceptable compression when an absolute value of a cumulated lateral displacement for said plurality of RF frame data is less than a threshold value across said lateral displacement, and a cumulated axial displacement for said plurality of RF frame data is greater than a lower threshold boundary and less than an upper threshold boundary across an axial displacement, wherein said cumulated axial displacement is a negative value.

48. The article of manufacture of claim 42, wherein said set of instructions to determine said acceptable compression value comprises
a set of instructions to achieve an acceptable compression when an absolute value of a cumulated lateral displacement for said plurality of RF frame data is less than a threshold value across said lateral displacement, and a cumulated axial displacement for said plurality of RF frame data is greater than a upper threshold boundary across an axial displacement, wherein said cumulated axial displacement is a negative value.

49. The article of manufacture of claim 42, further comprising a set of instructions to generate an elasticity image of said biological tissue based upon achieving an acceptable compression prior to executing said instruction to display said elasticity image.

50. A program storage device readable by machine, tangibly embodying a program of instructions executable by the machine to perform method steps for performing elasticity imaging on an ultrasound image, comprising:
setting a region of interest about an ultrasound image using a compression fixture;
compressing cyclically a biological tissue using said compression fixture;
acquiring at least one of a plurality of RF frame data at an imaging-relevant frame rate;
analyzing said at least one of said plurality of RF frame data using a compression feedback algorithm;
displaying a comparison of a quantitative indication of said at least one of said plurality of RF frame data across at least one displacement to a threshold value across said at least one displacement;
determining an acceptable compression value based upon said comparison; and
displaying an elasticity image of said biological tissue at said imaging-relevant frame rate.

51. The program storage device of claim 50, wherein analyzing said at least one of said plurality of RF frame data using said compression feedback algorithm comprises
selecting a first RF frame data of said plurality of RF frame data as a reference RF frame for said plurality of RF frame data;
comparing said plurality of RF frame data following said reference RF frame with said reference RF frame using a block matching algorithm;
performing said comparison step across an axial displacement and a lateral displacement;
determining a quantitative indication of a tissue compression quality for each of said plurality of RF frame data across a lateral displacement and an axial displacement; and
averaging said quantitative indications for said plurality of RF frame data across said lateral displacement and said axial displacement and generating a cumulated lateral displacement and a cumulated axial displacement for said plurality of RF frame data.

52. The program storage device of claim 50, wherein displaying visually said comparison comprises
displaying a comparison of a cumulated lateral displacement for said plurality of RF frame data to a threshold value across a lateral displacement; and
displaying a comparison of a cumulated axial displacement for said plurality of RF frame data to a threshold value across an axial displacement.

53. The program storage device of claim 50, wherein determining said acceptable compression value comprises
achieving an acceptable compression when an absolute value of a cumulated lateral displacement for said plurality of RF frame data is less than a threshold value across said lateral displacement, and a cumulated axial displacement for said plurality of RF frame data is less than an upper threshold boundary and greater than a lower threshold boundary across an axial displacement.

54. The program storage device of claim 50, wherein determining said acceptable compression value comprises
achieving an acceptable compression when an absolute value of a cumulated lateral displacement for said plurality of RF frame data is less than a threshold value across said lateral displacement, and a cumulated axial displacement for said plurality of RF frame data is less than a lower threshold boundary across an axial displacement, wherein said cumulated axial displacement is a positive value.

55. The program storage device of claim 50, wherein determining said acceptable compression value comprises
achieving an acceptable compression when an absolute value of a cumulated lateral displacement for said plurality of RF frame data is less than a threshold value across said lateral displacement, and a cumulated axial displacement for said plurality of RF frame data is greater than a lower threshold boundary and less than an upper threshold boundary across an axial displacement, wherein said cumulated axial displacement is a negative value.

56. The program storage device of claim 50, wherein determining said acceptable compression value comprises
achieving an acceptable compression when an absolute value of a cumulated lateral displacement for said plurality of RF frame data is less than a threshold value across said lateral displacement, and a cumulated axial displacement for said plurality of RF frame data is greater than an upper threshold boundary across an axial displacement, wherein said cumulated axial displacement is a negative value.

57. The program storage device of claim 50, further comprising the additional step of generating an elasticity image of said biological tissue based upon achieving an acceptable compression prior to displaying said elasticity image.

* * * * *